United States Patent [19]
Powell

[11] 4,414,397
[45] Nov. 8, 1983

[54] PRODUCTION OF ALKENYL SUBSTITUTED ALIPHATIC DICARBOXYLIC ANHYDRIDES

[75] Inventor: Justin C. Powell, Fairfax, Va.

[73] Assignee: Texaco Inc., White Plains, N.Y.

[21] Appl. No.: 337,564

[22] Filed: Jan. 7, 1982

[51] Int. Cl.³ .......................................... C07D 307/60
[52] U.S. Cl. ................................... 549/255; 549/231
[58] Field of Search ................................ 549/255, 231

[56] References Cited

U.S. PATENT DOCUMENTS 2,411,215 11/1946 Kise et al. ............................ 549/255
3,202,679 8/1965 Andrewsen et al. ............... 549/255
3,927,041 12/1975 Cengel et al. ....................... 549/255
4,110,349 8/1978 Cohen ................................... 549/255

Primary Examiner—Henry R. Jiles
Assistant Examiner—Bernard Dentz
Attorney, Agent, or Firm—Carl G. Ries; Robert A. Kulason; Carl G. Seutter

[57] ABSTRACT

Reaction of maleic acid anhydride and polyisobutylene to form product polyisobutenyl succinic acid anhydride is effected under controlled conditions whereby tar and sludge formation is minimized.

17 Claims, No Drawings

PRODUCTION OF ALKENYL SUBSTITUTED ALIPHATIC DICARBOXYLIC ANHYDRIDES

FIELD OF THE INVENTION

This invention relates to the preparation of product alkenyl-substituted aliphatic dicarboxylic acid anhydrides. More particularly it relates to preparation of these products under conditions whereby the amount of by-product formed is decreased.

BACKGROUND OF THE INVENTION

Alkenyl succinic acid anhydride type compounds may be typically prepared by the reaction of a polyisobutene and maleic acid anhydride, in the presence of catalyst such as 1,3-dibromo-5,5-dialkyl hydantoin. It is found however that the reaction mixture contains undesirable sludge in amount as high as 6–7 w % or more.

It is an object of this invention to provide a process for preparing alkenyl succinic acid anhydrides in the presence of catalyst which permits operation characterized by formation of decreased amounts of sludge. Other objects will be apparent to those skilled in the art.

STATEMENT OF THE INVENTION

In accordance with certain of its aspects, the method of this invention is directed to preparing a product alkenyl-substituted aliphatic dicarboxylic acid anhydride which comprises maintaining at 150° C.–300° C. a reaction mixture containing a molten olefin oligomer of molecular weight $\overline{M}_n$ of 500–30,000, containing 5–200 ppm of 1,3-dibromo-5,5-dialkyl-substituted hydantoin catalyst wherein the alkyl substituents contain a total of 2–21 carbon atoms; adding an unsaturated aliphatic dicarboxylic acid anhydride to said reaction mixture containing said molten olefin oligomer over a reaction period during which said olefin oligomer and said unsaturated aliphatic dicarboxylic acid anhydride react to form product alkenyl-substituted aliphatic dicarboxylic acid anhydride; controlling the rate of addition of said unsaturated aliphatic dicarboxylic acid anhydride whereby unreacted unsaturated aliphatic dicarboxylic acid anhydride in said reaction mixture is present in amount less than about its maximum solubility in said reaction mixture at the conditions of reaction and the reaction mixture is maintained as a substantially homogeneous reaction mixture of one phase; and recovering product alkenyl-substituted aliphatic dicarboxylic acid anhydride containing decreased quantities of unsaturated aliphatic dicarboxylic acid anhydride decomposition products.

DESCRIPTION OF THE INVENTION

The unsaturated aliphatic dicarboxylic acid anhydrides which may be employed to form the desired alkenyl-substituted saturated aliphatic dicarboxylic acids in practice of this invention may be intramolecular anhydrides typified by the following:

TABLE

| | |
|---|---|
| maleic | anhydride |
| citraconic | anhydride |
| itaconic | anhydride |
| ethylmaleic | anhydride |
| halo(eg chloro)maleic | anhydride |
| glutaconic | anhydride |
| homeosaconic | anhydride, etc. |

The preferred anhydride may be maleic anhydride.

The olefin oligomer, or polyolefin, reactant which may be employed may typically be an oligomer of a $C_2$–$C_8$ olefin having a molecular weight $\overline{M}_n$ of about 250–30,000, more commonly about 300–3000, say 1050–1400. The preferred oligomers are the polyisobutylenes, more preferably polyisobutylene of $\overline{M}_n$ of 250–5000, say 300–3000.

The polybutenes which may be employed may include those polymers obtained by polymerizing refinery streams containing eg isobutylenes, cis-butene-2,trans-butene-2, and butene-1. Polymerization of such streams, typically by use of a Friedel-Craft catalyst, permits attainment of a polyisobutylene of $\overline{M}_n$ of 250–5000, preferably 500–2000, say 700–1500, typically 1050–1400, and a viscosity of 4–5500 centistokes at 100° C. Molecular weight $\overline{M}_n$ may be determined by ASTM D-2503 method.

Reaction between the polyolefin and the unsaturated aliphatic dicarboxylic acid anhydride to form the desired product alkenyl saturated aliphatic dicarboxylic acid anhydride may be carried out at 150° C.–300° C. preferably about 210° C.–245° C., say about 245° C. for 2–10, preferably 4–10, say 6 hours at autogenous pressures in batch operation or at 150° C.–300° C., preferably 230° C.–260° C., say about 250° C. for 1–3 hours in a continuous process.

The brominated dialkylhydantoin which may be employed as catalyst in the process of this invention may include 1,3-dibromo-5,5-dialkylhydantoins, preferably those bearing $C_1$–$C_{10}$ alkyl groups. The alkyl groups preferably contain a total of 2–21 carbon atoms. Typical of the alkyl groups may be:

TABLE methyl
ethyl
propyls
butyls
amyls
hexyls
octyls
decyls
octadecyls etc.

The preferred hydantoin may be 1,3-dibromo-5,5-dimethylhydantoin.

In practice of the process of this invention, there may be added to a reaction mixture 0.25–2 parts, preferably 0.5–1.0 parts, say 1 part of the olefin oligomer, preferably polyisobutylene, and 15–150 parts per million, preferably 30–120 parts, per million, say 90 parts per million of the 1,3-dibromo-5,5-dialkyl-substituted hydantoin. The reaction mixture is maintained at 150° C.–300° C., preferably about 210° C.–245° C., say about 245° C. during the course of the reaction.

The unsaturated aliphatic dicarboxylic acid anhydride, preferably maleic acid anhydride in amount corresponding to a mole ratio (based on olefin) of 1–2:1 preferably 1.2–1.8:1, say 1.5:1 is added to the reaction mixture. It is preferred that the anhydride be at the temperature of the reaction mixture as it is added.

It is a feature of the process of this invention that the rate of addition of the unsaturated aliphatic dicarboxylic acid anhydride be controlled whereby unreacted aliphatic dicarboxylic acid anhydride in the reaction mixture is present in amount less than about its maximum solubility in the reaction mixture at the conditions of reaction and the reaction mixture is maintained as a substantially homogeneous reaction mixture of one phase.

It has been observed that the anhydride, typically maleic acid anhydride, is not very soluble in the oligomer reactant or in the product alkenyl-substituted aliphatic dicarboxylic acid anhydride of the reaction mixture. If 100% of the maleic acid anhydride to be employed in the reaction is added at the beginning of the reaction (as is true of prior art procedures), it is found that it does not entirely dissolve in the reaction mixture but forms a separate lower phase; and it appears that presence of this two-phase system containing undissolved maleic acid anhydride is correlative with production of undesirable sludge or tar with resulting lower yield of desired product.

It will be apparent to those skilled in the art that the maximum solubility of eg the maleic acid anhydride in the reaction mixture may depend upon many factors including reaction temperature, reaction pressure, molecular weight of the oligomer, the extent of reaction (i.e. the concentration of desired product typically polyisobutenyl succinic acid anhydride) etc. Generally it is observed that maleic acid anhydride is not very soluble in pure polybutylene oligomer, in pure polyisobutenyl succinic acid anhydride, or in mixtures thereof; and none of these non-polar materials is very soluble in pure maleic acid anhydride. The solubility of maleic acid anhydride in the product alkenyl succinic acid anhydride is greater than the solubility thereof in the polybutylene oligomer. At 60° F. for example maleic acid anhydride is found to be in solution in amount of 15.80% of Indopol L-14 brand of polyisobutylene ($\overline{M}_n$ of 320) and in amount of 5.0 v % of Indopol H-300 brand of polyisobutylene ($\overline{M}_n$ of 1290).

It will be apparent to those skilled in the art that the composition of the reaction mixture changes over the course of the reaction—and that at the beginning of the reaction period, it may be substantially all oligomer. As the reaction progresses the concentration of oligomer decreases and the concentrations of unreacted maleic acid anhydride and product alkenyl succinic acid anhydride may increase. Thus the concentration of maleic acid anhydride which is significant is that above which its solubility in the actual reaction mixture is so low that a two phase mixture forms. Maintaining the amount of unreacted maleic acid anhydride at concentration below this level will permit maintenance of the desired single phase system.

It will also be apparent that this level of "maximum solubility" may vary depending of course on the temperature of the reaction, the pressure of reaction, and other variables. Thus as a practical matter, the "maximum solubility" is not that level at which pure maleic acid anhydride is soluble in a pure oligomer—but rather the level above which, as empirically determined, two liquid phases form in this reaction system.

This may be determined in practice by withdrawing a portion of reaction mixture at a given time in a preliminary run and determining from the withdrawn sample, whether or not the reaction mixture is homogeneous. If for example, the withdrawn sample at time zero (after equilibration) is homogeneous this indicates that under the then prevailing conditions of operation, the initially added amount of maleic acid anhydride is within the desired range i.e. in amount less than about its maximum solubility. Of course, if the withdrawn sample shows evidence of two phases, then the amount of anhydride added is too great; and in subsequent trials, it will be decreased so that the amount added at time zero be within the desired range. In practice a few preliminary runs will readily establish a sequence of operations (i.e. a determination of how many separate aliquots and the amount of each as a percentage of the total) which may be followed in plant runs. During actual plant runs, a run may be monitored by withdrawing samples to insure that the system is homogeneous during operation.

In practice of this invention, it is thus found desirable to add the maleic acid anhydride over the course of the reaction rather than completely at the beginning as is common in the prior art. This may be done either continuously or in aliquots. In any event, it is desirable that the initial concentration of maleic acid anhydride added at the beginning of the addition in a preferred embodiment be less than about 75 mole %, preferably about 50 mole %-70 mole %, of the total of anhydride to be added as this generally corresponds to the maximum solubility in the reaction mixture at the typical conditions of reaction.

When the maleic acid anhydride is added continuously, the initial amount added may be about 53 mole % (of the total anhydride to be added) and the rate of addition may decrease during the course of the reaction.

In another embodiment, the maleic acid anhydride may be added in equal aliquots. The first aliquot may be sufficient to provide say 5-50 mole % of the total to be added. and later aliquots may be added at equal intervals in equal amounts subject to maintenance of the concentration of maleic acid anhydride in the desired range.

Typically the anhydride may be added in 2-10, preferably 3-6, say 5 aliquots over the course of the reaction time. In one embodiment, the total reaction time may be divided into five periods; and addition of equal amounts may be made at the beginning of each of these periods.

Practice of this mode of operation insures that the concentration of maleic acid anhydride is maintained at an amount slightly less than its maximum solubility in the reaction mixture at the conditions of operation and the reaction mixture is maintained as a substantially homogeneous reaction mixure of one phase.

In one preferred mode of operation wherein the total amount of the maleic acid anhydride to be added is 1.5 moles per mole of oligomer, the anhydride may be added in five aliquots at equal intervals of 1.5 hours. At time 0, there may be added 0.8 moles; at time 1.5 hours, there may be added 0.4 moles; at time 3.0 hours there may be added 0.2 moles; and at time 4.5 hours there may be added 0.1 moles the reaction mixture being maintained under reaction conditions for an additional 1.5 hours—making a total of 1.5 moles added over a six hour reaction time.

It is a feature of the process of this invention that the time of reaction may be decreased from the 10-18 hours, preferably 10-14 hours, say 11 hours which typify prior art batch operations to a level of 2-10 hours, preferably 4-10 hours, say 6 hours.

Although the process of this invention will permit attainment of improvement if the maleic acid anhydride be added so that it is present in amount much below its maximum solubility, it is preferred that it be present at a level which is about 80%-90% of the maximum solubility. Clearly higher concentrations up to 100% may be employed but this runs the risk of production of undesired amounts of sludge.

It is a feature of the process of this invention, that it is possible to prepare product alkenyl succinic acid anhydride containing sludge (as determined by standard procedures known to those skilled in the art) in amounts as low as 0.6 w %. Comparable control processes wherein the maleic acid anhydride is added in one aliquot at the beginning of the reaction give products containing 5 w %–20 w %, say 6 w % or more sludge.

It is also a feature of the process of this invention that it permits attainment of a given amount of product alkenyl succinic acid anhydride by the use of a lesser quantity of maleic acid anhydride—due in part at least to the more efficient use of maleic anhydride. This invention permits operation with mole ratio of maleic acid anhydride:olefin reactant of 2-1:1, preferably 1.8-1.1:1, say 1.5:1. Typical prior art processes employ mole ratios of 4-1:1, preferably 3-1:1, say 2:1.

Thus reaction may be effected under the following conditions:

TABLE

| | Broad | Preferred | Typical |
| --- | --- | --- | --- |
| Olefin parts | 100–500 | 200–300 | 260 |
| Anhydride parts | 10–50 | 20–30 | 29.72 |
| Mole ratio (final) | | | |
| Anhydride-olefin | 1–4:1 | 1.1–2:1 | 1.5;1 |
| Anhydride aliquots | 1–10 | 2–6 | 4* |
| Temperature °C. | 200–300 | 235–260 | 245 |
| Catalyst parts $\times 10^3$ | 7.8–46.8 | 14–31.2 | 23.4 |

*decreasing 50 w % each time

Work-up of the product may be carried out by distillation of unreacted maleic acid anhydride followed by filtration of the reaction product.

It is thus apparent that practice of the process of this invention permits attainment of the following advantages:
(i) attainment of product containing decreased amounts of sludge and tar;
(ii) operation for shorter reaction times;
(iii) consumption of lesser amounts of maleic anhydride;
(iv) substantially decreased work-up time due to decreased sludge content;
(v) substantially less autogenous pressure; etc.

DESCRIPTION OF PREFERRED EMBODIMENTS

Practice of the process of this invention will be apparent to those skilled in the art from the following examples wherein, as elsewhere in this specification, all parts are parts by weight unless otherwise stated.

EXAMPLE I*

In this control example which shows a typical prior art process, 44.6 parts of maleic acid anhydride (ca 0.4 moles) are added to a reaction vessel together with 260 parts (0.2 moles) of Indopol H-300 brand of polyisobutylene ($\overline{M}_n$ of 1290) oligomer. Mole ratio of anhydride to oligomer is ca 2:1. 0.0234 parts of 1,3-dibromo-5,5-dimethyl hydantoin is added. The total reaction mixture occupies 75 w % of the vessel.

The mixture is heated to 245° C. with agitation for 10 hours at 37 psig. At the end of this time, the reaction mixture is subjected to distillation at atmospheric pressure to remove unreacted maleic anhydride. The reaction mixture is then filtered (hot). Product alkenyl succinic acid anhydride is recovered. The filter cake (tar and sludge) is 20 parts.

EXAMPLE II

In this Example which represents practice of a preferred embodiment of this invention, there are added to a reaction vessel 260 parts (0.2 moles) of Indopol H-300 brand of polyisobutylene ($\overline{M}_n$ of 1290) oligomer and 0.0234 parts of 1,3-dibromo-5,5-dimethyl hydantoin catalyst.

The mixture is heated to 245° C. at 37 psig. At a time denoting the beginning of reaction, 15.85 parts (0.8 moles per moles of oligomer) of molten maleic acid anhydride are admitted in a first aliquot. The mixture is heated with agitation for 1.5 hours. At 1.5 hours, there are added 7.925 parts of maleic acid anhydride (0.4 moles per moles of oligomer); at 3 hours there are added 3.963 parts (0.2 moles per moles of oligomer) of maleic acid anhydride; at 4.5 hours there are added 1.982 parts (0.1 moles per moles of oligomer) of maleic acid anhydride making a total of 29.72 parts of maleic acid anhydride, corresponding to a mole ratio of maleic acid anhydride to oligomer of 1.5:1.

At the end of the reaction time of 6 hours total, the reaction mixture is subjected to distillation at atmospheric pressure to remove unreacted maleic acid anhydride. The reaction mixture is then filtered (hot) to recover 2 parts of tar and sludge as filter cake. Product polyisobutenyl succinic acid anhydride is recovered as filtrate.

It is apparent from a comparison of Examples I* and II that the sludge content has decreased from 20 parts down to 2 parts. Higher, more efficient, utilization of maleic acid anhydride is evidenced by the recovery of unreacted material from the Experimental Example II in lesser amounts than that recovered from Control Example I. The time of reaction (6 hours) for Example II is desirably shorter than is that of Example I* (10 hours).

Although this invention has been illustrated by reference to specific embodiments, it will be apparent to those skilled in the art that various changes and modifications may be made which clearly fall within the scope of this invention.

I claim:
1. The method of preparing a product alkenyl-substituted aliphatic dicarboxylic acid anhydride, by reaction of components consisting essentially of olefin oligomer and unsaturated dicarboxylic acid anhydride in the presence of 1,3-dibromo-5,5-dialkyl substituted hydantoin catalyst, which comprises
    maintaining at 150° C.–300° C. a reaction mixture containing a molten olefin oligomer of molecular weight $\overline{M}_n$ of 500–30,000, containing 5–200 ppm of 1,3-dibromo-5,5-dialkyl-substituted hydantoin catalyst wherein the alkyl substituents contain a total of 2–21 carbon atoms;
    adding an unsaturated aliphatic dicarboxylic acid anhydride to said reaction mixture containing said molten olefin oligomer over a reaction period during which said olefin oligomer and said unsaturated aliphatic dicarboxylic acid anhydride react to form product alkenyl-substituted aliphatic dicarboxylic acid anhydride;
    controlling the rate of addition of said unsaturated aliphatic dicarboxylic acid anhydride whereby unreacted unsaturated aliphatic dicarboxylic acid anhydride in said reaction mixture is present in amount less than about its maximum solubility in said reaction mixture at the conditions of reaction and the reaction mixture is maintained as a substantially homogeneous reaction mixture of one phase; and recovering product alkenyl-substituted aliphatic dicarboxylic acid anhydride containing decreased quantities of unsaturated aliphatic dicarboxylic acid anhydride decomposition products.

2. The method of preparing a product alkenyl-substituted aliphatic dicarboxylic acid anhydride as claimed in claim 1 wherein said oligomer has a molecular weight $\overline{M}_n$ of 500–5000.

3. The method of preparing a product alkenyl-substituted aliphatic dicarboxylic acid anhydride as claimed in claim 1 wherein said oligomer has a molecular weight of 500–3000.

4. The method of preparing a product alkenyl-substituted aliphatic dicarboxylic acid anhydride as claimed in claim 1 wherein said oligomer is a polyisobutylene.

5. The method of preparing a product alkenyl-substituted aliphatic dicarboxylic acid anhydride as claimed in claim 1 wherein said catalyst is 1,3-dibromo-5,5-dimethyl hydantoin.

6. The method of preparing a product alkenyl-substituted aliphatic dicarboxylic acid anhydride as claimed in claim 1 wherein said unsaturated aliphatic dicarboxylic acid anhydride is maleic acid anhydride.

7. The method of preparing a product alkenyl-substituted aliphatic dicarboxylic acid anhydride as claimed in claim 1 wherein said unreacted unsaturated aliphatic dicarboxylic acid anhydride is present in the reaction mixture in amount of about 80%–90% of its solubility therein.

8. The method of preparing a product alkenyl-substituted aliphatic dicarboxylic acid anhydride as claimed in claim 1 wherein said reaction period is 1–10 hours.

9. The method of preparing a product alkenyl-substituted aliphatic dicarboxylic acid anhydride as claimed in claim 1 wherein said unsaturated aliphatic dicarboxylic acid anhydride is added in a plurality of aliquots during the reaction period.

10. The method of preparing a product alkenyl-substituted aliphatic dicarboxylic acid anhydride as claimed in claim 1 wherein unsaturated aliphatic dicarboxylic acid anhydride is added in a plurality of equal aliquots during the reaction period.

11. The method of preparing a product alkenyl-substituted aliphatic dicarboxylic acid anhydride as claimed in claim 1 wherein said unsaturated aliphatic dicarboxylic acid anhydride is added in 3–10 aliquots during the reaction period.

12. The method of preparing a product alkenyl-substituted aliphatic dicarboxylic acid anhydride as claimed in claim 1 wherein said unsaturated aliphatic dicarboxylic acid anhydride is added continuously during the reaction period.

13. The method of preparing a product alkenyl-substituted aliphatic dicarboxylic acid anhydride as claimed in claim 1 wherein said unsaturated aliphatic dicarboxylic acid anhydride is added continuously, the plot of total amount added as a function of time being linear.

14. The method of preparing a product alkenyl-substituted aliphatic dicarboxylic acid anhydride as claimed in claim 1 wherein said unsaturated aliphatic dicarboxylic acid anhydride is added continuously, the plot of amount added at a given time as a function of time being linear with a slight downward slope.

15. The method of preparing a product alkenyl-substituted aliphatic dicarboxylic acid anhydride as claimed in claim 1 wherein said unsaturated aliphatic dicarboxylic acid anhydride is added in amounts each of which is one-half that of the prior amount.

16. The method of preparing a product alkenyl-substituted aliphatic dicarboxylic acid anhydride as claimed in claim 15 wherein said unsaturated aliphatic dicarboxylic acid anhydride is added in four aliquots of 0.8 moles, 0.4 moles, 0.2 moles, and 0.1 moles—per mole of oligomer.

17. The method of preparing a product alkenyl-substituted succinic anhydride, by reaction of components consisting essentially of olefin oligomer and unsaturated dicarboxylic acid anhydride in the presence of 1,3-dibromo-5,5-dialkyl substituted hydantoin catalyst, which comprises maintaining at 150° C.–300° C. a reaction mixture containing a molten polybutylene, $\overline{M}_n$ of 500–3000, containing 5–200 ppm of 1,3-dibromo-5,5-dialkyl-substituted hydantoin catalyst wherein the alkyl substituents contain a total of 2–21 carbon atoms;

adding maleic acid anhydride to said molten polybutylene over a reaction period during which said polybutylene and said maleic acid anhydride react to form product alkenyl-substituted succinic anhydride;

controlling the rate of addition of said maleic acid anhydride whereby unreacted maleic acid anhydride in said reaction mixture is present in amount less than about its maximum solubility in said reaction mixture at the conditions of reaction and the reaction mixture is maintained as a substantially monogeneous reaction mixture of one phase; and recovering product alkenyl-substituted succinic anhydride containing decreased quantities of maleic acid anhydride decomposition products.

* * * * *